United States Patent

Ma et al.

Patent Number: 5,973,185
Date of Patent: Oct. 26, 1999

[54] METHOD FOR PREPARING α-CHLOROBORONIC ACIDS FROM MANNITOL

[75] Inventors: Philip Ma, Chadds Ford, Pa.; Biao Jiang, Shanghai, China

[73] Assignee: DuPont Pharmaceuticals Company, Wilmington, Del.

[21] Appl. No.: 08/888,380

[22] Filed: Jul. 7, 1997

[51] Int. Cl.[6] ...................................................... C07F 5/04
[52] U.S. Cl. ........................ 558/288; 558/286; 558/298
[58] Field of Search ..................................... 558/288, 286, 558/298

[56] References Cited

PUBLICATIONS

CA; 99; 21568 abs of Trimethuylsileniol as a leaving group in preparative organic chem, Vorbrueggen Curr. Trends in Org. Synthesis Conf. 4th Int.

J. Wityak, R. A. Earl, M.M. Abelman, Y.B. Bethel, B.N. Fisher, G.S. Kauffman, C.A. Kettner, P. Ma, J.L. McMillan, L.J. Mersinger, J. Pesti, M.E. Pierce, F.W. Rankin, R.J. Chorvat and P.N. Confalone, *J. Org. Chem.* 1995, 60(12), 3717–3722, "Synthesis of Thrombin Inhibitor DuP 714".

R.W. Hoffmann and S. Dresely, *Synthesis* 1988, 103–105, "Preparation of 3–Substituted (E)–1–Alkenylboronic Esters".

R.W. Hoffmann and S. Dresely, *Agnew. Chem. Int. Ed. Engl.* 1986, 25(2), 189–190, "Optically Active α–Cloro–(E)–crotylboronate Esters by Allyl Rearrangement".

D.S. Matteson and K.M. Sadhu, *J. Am. Chem. Soc.* 1981, 103, 5241–5242, "(R)–1–Acetamido–2–phenylethanebornic Acid. A Specific Transition–State Analogue for Chymotrypsin".

B. Jiang and P. Ma, *Synthetic Communications*, 1995, 25(22), 3641–3645, "An Improved Synthesis of (+)–3, 4—Isopropylidene Butyne".

R.W. Hoffmann, S. Dresely and J.W. Lanz, *Chem. Ber.* 1988, 121, 1501–1507, "Addition of (α–Chlorocrotyl)boronates to aldehydes".

D.S. Matteson, *Chem. Rev.* 1989, 89, 1535–1551, "α–Halo Boronic Esters: Intermediates for Stereodirected Synthesis".

*Primary Examiner*—Gary Geist
*Assistant Examiner*—Jean F Vollano
*Attorney, Agent, or Firm*—David H. Vance

[57] ABSTRACT

A novel process for making compounds of Formula I,

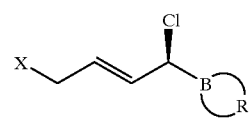

wherein X is a leaving group selected from the group Br, Cl, TsO, MsO, and TfO and R is a 1,2-diol, from a compound of Formula II:

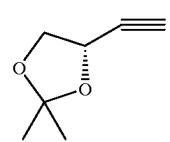

is described.

12 Claims, No Drawings

METHOD FOR PREPARING α-CHLOROBORONIC ACIDS FROM MANNITOL

FIELD OF THE INVENTION

The present invention relates generally to processes for the preparation of α-chloroboronic acids from mannitol, such α-chloroboronic acids being useful as intermediates for the synthesis of aminopeptidase inhibitors.

BACKGROUND OF THE INVENTION

Aminopeptidases are a group of metalloenzymes that catalyze the hydrolysis of the NH$_2$-terminal peptide bonds in polypeptides. A number of effective inhibitors have been reported for aminopeptidases (A. B. Shenvi, *Biochemistry* 1986, 25, 1286). A number of α-aminoboronic acids (i.e. DuP 714) and their derivatives have been reported as effective inhibitors for aminopeptidases by acting as "transition-state analogues."

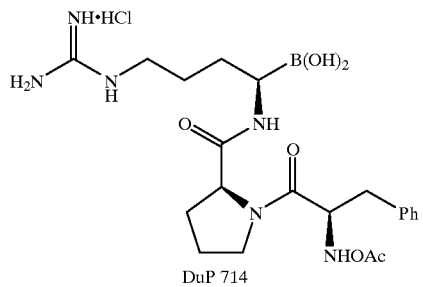
DuP 714

DuP 714 and its derivatives were first prepared (Wityak et al, *J. Org. Chem.* 1995, 60, 3717) using procedures developed by Matteson et al (*J. Am. Chem. Soc.* 1981, 103, 5241). The Matteson protocol is used to prepare α-amino or α-amido-boronic acids by assymetric homologation of ethylene glycol benzylboronate.

Wityak et al incorporated this technique using pinanediol 1-(3-bromopropyl)boronate (A) as the starting material to make an α-amino-boronic acid (C), which was used in the synthesis of DuP 714. Homologation occurred upon assymetric addition of (dichloromethyl)lithium to produce (B) and the chloride was displaced by nitrogen upon addition of lithiohexamethyldisilazane (KHDMS). This process uses expensive raw materials, low temperatures, and unfortunately requires difficult isolation and purification steps.

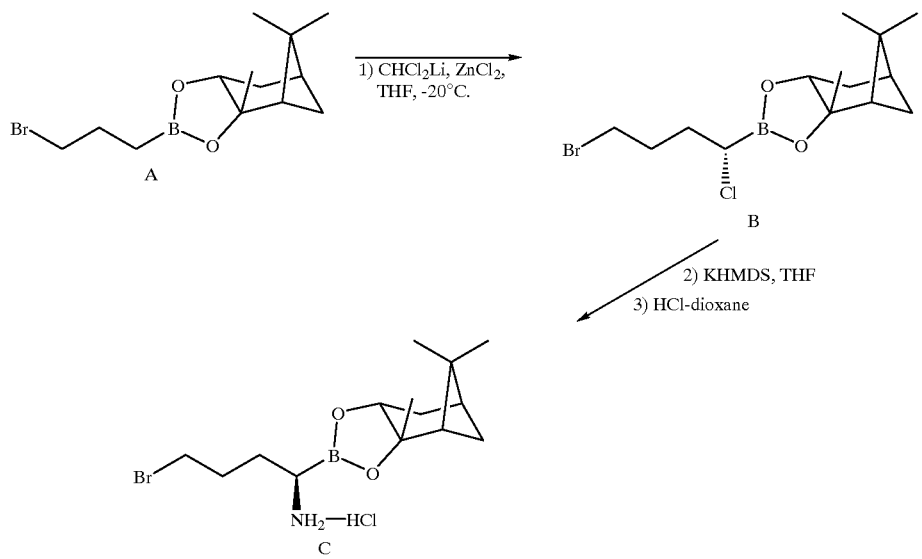

Hoffmann et al (*Angew. Chem. Int. Ed. Engl.* 1986, 25(2), 189-190) described the assymetric synthesis of α-(-chloro-(E)-crotylboronate esters via allyl rearrangement. Contacting pinacol 1-(3'-(S)-trimethylsiloxy)-butenylboronate (D) with thionyl chloride in petroleum ether formed pinacol α-chloro-(E)-crotylboronate (E) in 75% yield. Unfortunately, pinacol E cannot easily be manipulated to form a compound useful for the synthesis of DuP 714.

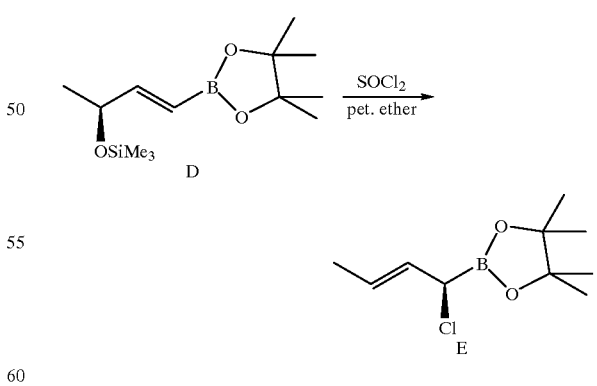

It is therefore desirable to find less expensive and simpler synthetic procedures for production of α-chloroboronic acids and their corresponding α-aminoboronic acids, which can be used as intermediates to form compounds such as DuP 714. Such procedures preferably should use readily available and inexpensive raw materials.

SUMMARY OF THE INVENTION

Accordingly, one object of the present invention is to provide a novel process for making α-chloroboronic acids.

Another object of the present invention is to provide novel α-chloroboronic acids of Formula I shown below.

These and other objects, which will become apparent during the following detailed description, have been achieved by the inventors' discovery that compounds of Formula I,

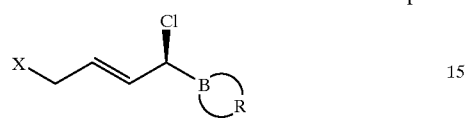

I wherein X is a leaving group selected from the group Br, Cl, TsO, MsO, and TfO and R is a 1,2-diol, are formed by a process, comprising:

(a) contacting a compound of Formula II:

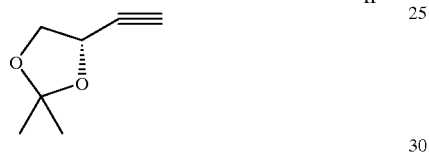

II with a dialkyl borane, oxidizing the resulting borane and, transesterifying the resulting boronate with a 1,2-diol to form a boronate of Formula III;

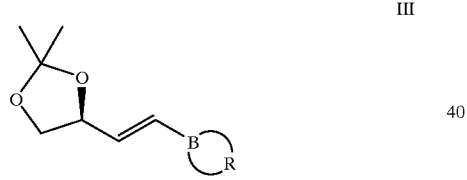

III (b) contacting a boronate of Formula III with an acidic medium to remove the acetonide protecting group and converting the resulting terminal alcohol to a leaving group to form a compound of Formula IV;

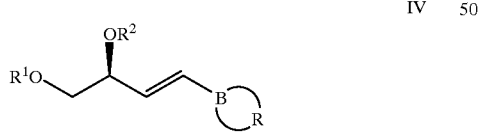

IV wherein R¹ is selected from the group Ts, Ms, and Tf, and R² is H; and, (c) contacting a compound of Formula IV with SOCl₂ in a suitable solvent to form a compound of Formula I.

DETAILED DESCRIPTION OF THE INVENTION

[1] Thus, is a first embodiment, the present invention provides a process for tne synthesis of α-chloroboronic acids of Formula I:

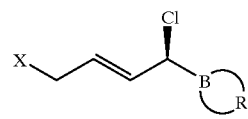

I wherein X is a leaving group selected from the group Br, Cl, TsO, MsO, and TfO and R is a 1,2-diol, comprising:

(b) contacting a boronate of Formula III;

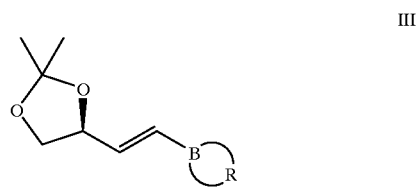

III with an acidic medium to remove the acetonide protecting group and converting the resulting terminal alcohol to a leaving group to form a compound of Formula IV;

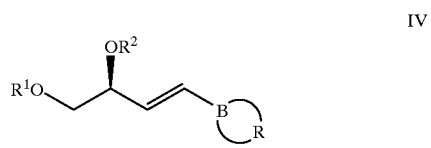

IV wherein $R^1$ is selected from the group Ts, Ms, and Tf, and $R^2$ is H; and, (c) contacting a compound of Formula IV with SOCl₂ in a suitable solvent to form a compound of Formula I.

[2] In a preferred embodiment, the compound of Formula III is formed by a process, comprising:

(a) contacting a compound of Formula II:

II with a dialkyl borane, oxidizing the resulting borane and, transesterifying the resulting boronate with a 1,2-diol to form a boronate of Formula III.

[3] In a more preferred embodiment, in step (a) the dialkyl borane is selected from (c-C₆H₁₁)₂BH, Disiamylborane, and 9-BBN.

[4] In another more preferred embodiment, the 1,2-diol is selected from catechol, pinacol and pinanediol.

[5] In an even more preferred embodiment, the 1,2-diol is pinacol.

[6] In another more preferred embodiment, in step (a) trimethylamine-N-oxide is used as the oxidizing agent.

[7] In another preferred embodiment, a compound of Formula I wherein X is other than a halogen is converted to a compound of Formula I wherein X is Cl by a process, comprising:

(d) contacting a compound of Formula I with pyridine-HCl.

[8] In a more preferred embodiment, step (d) is performed by direct addition of pyridine-HCl to the reaction mixture resulting from step (c).
[9] In another preferred embodiment, steps (b) and (c) are combined in one pot to form a compound of Formula I wherein X is Cl.
[10] In another preferred embodiment, a compound of Formula I is converted to a compound of Formula V;

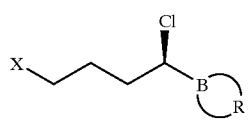

V by a process, comprising:
(e) hydrogenating a compound Formula I.
[11] In another more preferred embodiment, in step (e) ethyl acetate is used as solvent and $PtO_2$ as catalyst.
[12] In another preferred embodiment, in step (b) the acidic medium comprises methanol and trimethylchlorosilane, and $R^1$ is Ts.
[13] In another more preferred embodiment, in step (c) petroleum ether is used as solvent.
[14] In a second embodiment, the present invention provides novel compounds of Formula I:

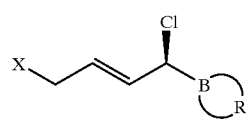

I wherein X is a leaving group selected from the group Cl, Br, TsO, MsO, and TfO and R is a diol selected from catechol, pinacol and pinanediol.
[15] In another preferred embodiment, R is pinacol or pinanediol.
[16] In another more preferred embodiment, R is pinacol.
[17] In an even more preferred embodiment, X is Cl.
[18] In an even more preferred embodiment, X is TsO.
[19] In an even more preferred embodiment, X is Br.

A 1,2-diol, as used herein, is a 1,2-dihydroxy compound capable of esterifying a borate and/or a boronate to form a five-membered cyclic boronate. One of skill in the art would recognize a wide variety of 1,2-dihydroxy compounds are capable of forming cyclic boronates. As used herein, a 1,2-diol is intended to encompass both alkyl and aryl diols. Examples of diols include, but are not intended to be limited to, ethylene glycol, catechol, pinacol and pinanediol.

A dialkyl borane as used herein is any dialkyl borane ($R'_2BH$) which will react with the alkyne of Formula II to form to form a compound which can then be oxidized, and if necessary transesterified, to form a compound of Formula III. Examples dialkyl boranes, include but are not intended to be limited to, 9-BBN, disiamylborane, and dicyclohexylborane, preferably dicyclohexylborane. Additional examples can be found in Pelter, A.; Smith, K.; Brown, H. C., *Borane Reagents*, pp. 179–193.

A reagent suitable to convert a hydroxyl group to a leaving group can be selected from a variety of such reagents as will be appreciated by one of skill in the art of organic synthesis. For example, such reagents may be selected from, but are not intended to be limited to, benzenesulfonyl chloride, dimethylbenzenesulfonyl chloride, trimethylbenzene sulfonyl chloride, chlorobenzenesulfonyl chloride, dichlorobenzenesulfonyl chloride, trichlorobenzenesulfonyl chloride, p-toluenesulfonyl chloride (TsCl), p-toluenesulfonic anhydride (TsOTs), methanesulfonyl chloride (MsCl), methanesulfonic anhydride (MsOMs), trifluoromethanesulfonyl chloride (TfCl), and trifluoromethanesulfonic anhydride (TfOTf).

The present invention is contemplated to be practiced on at least a multigram scale, kilogram scale, multikilogram scale, or industrial scale. Multigram scale, as used herein, is preferably the scale wherein at least one starting material is present in 10 grams or more, more preferably at least 50 grams or more, even more preferably at least 100 grams or more. Multikilogram scale, as used herein, is intended to mean the scale wherein more than one kilogram of at least one starting material is used. Industrial scale as used herein is intended to mean a scale which is other than a laboratory scale and which is sufficient to supply product sufficient for either clinical tests or distribution to consumers.

Synthesis

By way of example and without limitation, the present invention may be further understood by Scheme 1. This scheme details the general synthetic method for preparation of compounds of Formula I from compounds of Formulae II and III.

Scheme 1

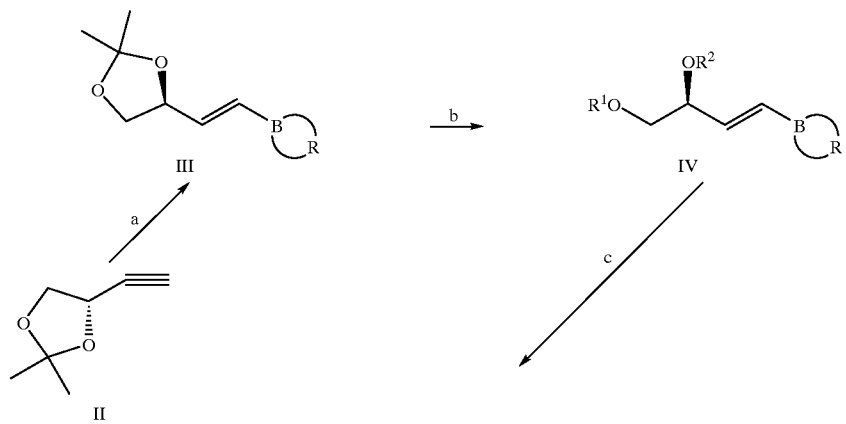

-continued

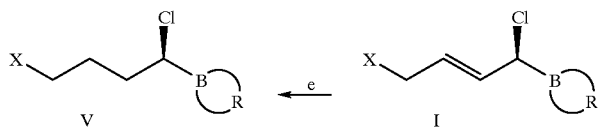

Step a:

The starting alkyne (II) is derived from mannitol using the procedure of Jiang, B.; Ma, P. *Synthetic Communications* 1995, 25, 3641. Alkyne II can be converted to III by addition of a dialkylborane, followed by oxidation of the resulting alkenylborane, and finally transesterification of the resulting boronate with an appropriate diol (see R. W. Hoffmann, R. W.; Dresley, S. *Synthesis* 1988, 103–105). The dialkylborane used can be selected from any dialkylborane ($R_2BH$) such as 9-BBN (9-borabicyclo[3.3.1]nonane) and dicyclohexylborane, preferably dicyclohexylborane. The oxidation is preferably performed using about 1, 1.5, 2, 2.5, or more equivalents of trimethylamine-N-oxide, more preferably about 2 equivalents are used. The diol used is preferably selected from pinacol, pinanediol, and catechol, more preferably pinacol. Solvents useful for this reaction include 1,2-dimethoxyethane (DME), DMSO, and $CH_2Cl_2$, preferably DME. The yield obtained is preferably at least 80%, more preferably 85%, even more preferably 90%, and even still more preferably 95%. The reaction is exothermic and is preferably run at the reflux point of the solvent used.

Step b:

The acetonide protecting group can be removed by contacting a compound of formula III with an acidic medium, Preferably an alcohol and a silane are used. Examples of alcohols include, but are not limited to, methanol, ethanol and isopropyl alcohol. Examples of silanes include, but are not limited to, trimethylchlorosilane and diphenylmethylchlorosilane. Preferably methanol and trimethylchlorosilane are used in combination. The deprotection is preferably run at ambient temperature and can be monitored using standard TLC techniques. Other deprotection methods can be used, see for example T. W. Green & P. G. M. Wuts, *Protecting Groups in Organic Synthesis* 2nd ed, pp. 125-126 (1991)

Removal of the acetonide protecting group leaves two hydroxy groups, a terminal alcohol and a secondary alcohol. Compound IV can then be formed by converting the terminal alcohol into a leaving group by reaction with an alcohol leaving group forming compound. Preferably from 1–10, more preferably from 1–2 equivalents of alcohol leaving group forming compound are used. Examples of an alcohol leaving group forming compound include, but are not limited to, p-toluenesulfonyl chloride (TsCl), p-toluenesulfonic anhydride (TsOTs), methanesulfonyl chloride (MsCl), methanesulfonic anhydride (MsOMs), trifluoromethanesulfonyl chloride (TfCl), and trifluoromethanesulfonic anhydride (TfOTf). A base can be used to drive the reaction. Examples of bases include, but are not limited to, triethylamine, DMAP (4-dimethylaminopyridine), DBU (1,8-diazabicyclo[5.4.0]undec-7-ene), DBN (1,5-diazabicyclo[4.3.0]non-5-ene), pyridine, collidine, and lutidine. Preferably pyridine is used. Preferably this reaction is run from about −10 to 25° C., more preferably about 0° C. Reaction times may vary depending on choice of reagents, but are preferably from about 4–30 hours, more preferably from 8–24 hours. Aprotic solvents such as ethers (e.g., dimethyl ether and diethyl ether), dichloromethane, chloroform or benzene are preferably used. The overall yield obtained from this step is preferably at least 80%, more preferably 85%, even more preferably 90%, and even still more preferably 95%.

Step c:

Conversion of IV to I involves a rearrangement which is effected using thionyl chloride. Optionally a catalytic amount of a catalyst such as $Co(NO_3)_2$ can be added to the reaction. As solvent, preferably an ether selected from dimethyl ether, diethyl ether or petroleum ether, toluene, benzene, and methylene chloride, more preferably petroleum ether is used. The rearrangement is preferably run at from 0–25° C., more preferably ambient temperature. The selectivity of the reaction is preferably at least 20:1, more preferably at least 25:1, and even more preferably at least 26:1 of desired isomer versus undesired isomer. The yield obtained is preferably at least 80%, more preferably 85%, even more preferably 90%, and even still more preferably 95%.

Step d(not shown in Scheme 1):

Conversion of compounds wherein X is other than a halogen to compounds wherein X is Cl can be carried out by treatment with pyridine-HCl at ambient temperature. Non-nucleophilic solvents like those defined in Step c are generally useful. The reaction is preferably run at ambient temperature for from about 1–10 hours, more preferably about 2–5 hours. Preferably this step is run after Step c, but before removal of the solvent used in Step c. Thus, loss of product and need for additional solvent can be minimized.

Similarly, when X is other than a halogen, conversion to compounds wherein X is Br can be obtained using pyridine-HBr.

Step e:

Hydrogenation of I to V can be achieved using a catalyst, hydrogen gas and a solvent. Examples of catalysts include, but are not limited to, Pd/C, $PtO_2$, and Ra—Ni, preferably $PtO_2$. Preferably the solvent is selected from ethanol, methanol, and ethyl acetate, more preferably ethyl acetate. This step is preferably performed at room temperature.

The α-chloro group of a compound of Formula V can be converted to an amino group as described for conversion of compound B to C in the Background of this application (i.e., by using lithium hexamethyldisilazide). One of ordinary skill in the art would recognize how to further convert this amino compound to DuP 714 based on the description provided by Wityak et al, *J. Org. Chem.* 1995, 60, 3717.

One-pot conversion of III to I, wherein X is Cl, can be achieved by combining the deprotection and leaving group formation procedures of Step b and the rearrangement protocol of Step c. This one-pot reaction can be advantageous as it minimizes repeated isolation steps which saves time and solvents and limits product loss during isolation. Since use of thionyl chloride produces HCl and pyridine can be used as base in Step b, pyridine-HCl is expected to be present in the one-pot conversion and the end product contains X as Cl. If this is desirable, one can minimize solvents, time, and loss of product by using this one-pot procedure.

Other features of the invention will become apparent in the course of the following descriptions of exemplary embodiments which are given for illustration of the invention and are not intended to be limiting thereof.

EXAMPLES

Example 1

Preparation of [S-(E)]-2-[2-(2,2-dimethyl-1,3-dioxolan-4-yl)ethenyl]-4,4,5,5-tetramethyl-1,3,2-dioxaborolane To a solution of 50 mmol (10M, 5mL) of dimethylsulfide-borane complex in 60 mL of DME under $N_2$ at 0° C. was added cyclohexene (8.2 g, 10.1 mL, 100 mmol). After 15 minutes, the mixture was warmed to room temperature and stirred for 1 hour. The reaction was again cooled down to 0° C., and (S)-4-ethynyl-2,2-dimethyl-1,3-dioxolane (5.5 g (50 mmol) was added. After stirring at room temperature for 1 hour, trimethylamine N-oxide (7.5 g, 100 mmol) was dropwise added at a rate keeping the reaction under gentle reflux. After the addition, the reaction mixture was cooled to room temperature and pinacol (5.9 g, 50 mmol) was added. The reaction was stirred at room temperature overnight, filtered, and was concentrated at reduced pressure. The residue was distilled (175° C., 0.5 mm Hg, 90%) to afford the title compound (11 g) as a colorless oil: [M+H]+=255.3.

Example 2

Preparation of [S-(E)]-2-hydroxy-4-(4,4,5,5-tetramethyl-1,3,2-dioxaborolan-2-yl)-3-butenyl 4-methylbenzenesulfonate To a solution of [S-(E)]-2-[2-(2,2-dimethyl-1,3-dioxolan-4-yl)ethenyl]-4,4,5,5-tetramethyl-1,3,2-dioxaborolane (4.8 g 20 mmol) in MeOH (20 mL) was added trimethylchlorosilane (523 µl 4 mmol) at r.t. for 1 h. The reaction was concentrated to dryness under reduced pressure. The residue was washed with 10 mL of hexane/ether (10/1) and dried to afford 3.7 g (95%) solid diol intermediate.

To a solution of diol intermediate (392 mg 2 mmol) in 5 mL of dichloromethane containing pyridine (154 µl, 2 mmol) at 0° C. was added p-toluenesulfonyl chloride (390 mg, 2.05 mmol) after stirring for 1.5 h, the reaction was concentrated to dryness under reduced pressure. The residue was washed with 10 mL of ethylacetate/hexane (1/1) and filtered. The filtrate was concentrated and yielded the title compound (736.5 mg) as a colorless oil: [M+H]+=369.1.

Example 3

Preparation of [S-(E)]-4-chloro-4-(4,4,5,5-tetramethyl-1,3,2-dioxaborolan-2-yl)-2-butenyl 4-methylbenzenesulfonate To a solution of [S-(E)]-2-hydroxy-4-(4,4,5,5-tetramethyl-1,3,2-dioxaborolan-2-yl)-3-butenyl 4-methylbenzenesulfonate (736 mg, 2 mmol) and catalytic amount of $Co(NO_3)_2$ hexahydrate in petroleum ether (15 mL) at room temperature was added $SOCl_2$ (162 µL, 2 mmol). The reaction was stirred overnight. The solvent was removed under reduced pressure to give desired the title compound as a colorless oil.

Example 4

Preparation of [S-(E)]-2-(1,4-dichloro-2-butenyl)-4,4,5,5-tetramethyl-1,3,2-dioxaborolane To a solution of [S-(E)]-2-hydroxy-4-(4,4,5,5-tetramethyl-1,3,2-dioxaborolan-2-yl)-3-butenyl 4-methylbenzenesulfonate (3.68 g, 10 mmol) and catalytic amount of $Co(NO_3)_2$ hexahydrate in petroleum ether (250 mL) at r.t. was added $SOCl_2$ (900 µL, 12 mmol). The reaction was stirred at r.t. for 3 h before of pyridine hydrochloride (1.4 g, 12 mmol) was added. The reaction mixture was stirred for additional 3 h, and filtered, and the filtrate was concentrated to the title compound as colorless oil: [M+NH4]=268.

The product was directly reacted in Example 6 without further purification.

Example 5

Preparation of [S-(E)]-2-(1,4-dichloro-2-butenyl)-4,4,5,5-tetramethyl-1,3,2-dioxaborolane To a solution of [S-(E)]-4-chloro-4-(4,4,5,5-tetramethyl-1,3,2-dioxaborolan-2-yl)-2-butenyl 4-methylbenzenesulfonate in pet-ether was added pyridine-HCl (1.2 eq) at room temperature. The mixture was stirred at room temperature for 3 h, filtered, and the filtrate was concentrated to give the title compound as a colorless oil: [M+NH4]=268.

Example 6

Preparation of (S)-2-(1,4-dichlorobutyl)-4,4,5,5-tetramethyl-1,3,2-dioxaborolane A solution of [S-(E)]-2-(1,4-dichloro-2-butenyl)-4,4,5,5-tetramethyl-1,3,2-dioxaborolane from step 3a in ethylacetate (15 mL) was hydrogenated with 100 mg of $PtO_2$ under 70 psi H2 pressure for 3 h. The product was isolated by distillation (70° C., 0.05 mm Hg) to afford the title compound (1.5 g)as a colorless oil: [M+NH4]+=270.

Obviously, numerous modifications and variations of the present invention are possible in light of the above teachings. It is therefore to be understood that within the scope of the appended claims, the invention may be practiced otherwise that as specifically described herein.

What is claimed as new and desired to be secured by Letter Patent of United States is:

1. A process for the synthesis of α-chloroboronic acids of Formula I:

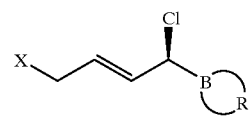

I wherein X is a leaving group selected from the group Br, Cl, p-toluenesulfonate, methanesulfonate, and trifluoromethanesulfonate and R is a 1,2-diol selected from catechol, pinacol and pinanediol, wherein the R is attached to B via its two oxygen moieties, comprising:

(b) contacting a boronate of Formula III;

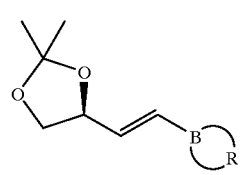

III with an acidic medium to remove the acetonide protecting group and converting the resulting terminal alcohol to a leaving group to form a compound of Formula IV;

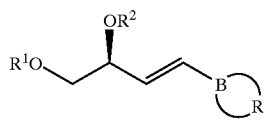

wherein R¹ is selected from the group p-toluenesulfonyl, methanesulfonyl, and trifluoromethanesulfonyl, and R² is H; and, (c) contacting a compound of Formula IV with $SOCl_2$ in a suitable solvent to form a compound of Formula I.

2. A process according to claim 1, wherein a compound of Formula I wherein X is other than a halogen is converted to a compound of Formula I wherein X is Cl by a process, comprising:

(d) contacting a compound of Formula I with pyridine-HCl.

3. A process according to claim 2, wherein step (d) is performed by direct addition of pyridine-HCl to the reaction mixture resulting from step (c).

4. A process according to claim 1, wherein steps (b) and (c) are combined in one pot to form a compound of Formula I wherein X is Cl.

5. A process according to claim 1, wherein in step (b) the acidic medium comprises methanol and trimethylchlorosilane, and R¹ is Ts.

6. A process according to claim 5, wherein in step (c) petroleum ether is used as solvent.

7. A compound of Formula I:

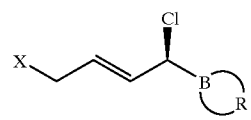

wherein X is a leaving group selected from the group Cl, Br, p-toluenesulfonate, methanesulfonate, and trifluoromethanesulfonate and R is a diol selected from catechol, pinacol and pinanediol, wherein the R is attached to B via its two oxygen moieties.

8. A compound according to claim 7, wherein R is pinacol or pinanediol.

9. A compound according to claim 8, wherein R is pinacol.

10. A compound according to claim 8, wherein X is Cl.

11. A compound according to claim 8, wherein X is p-toluenesulfonate.

12. A compound according to claim 8, wherein X is Br.

* * * * *